(12) United States Patent
Weilbacher et al.

(10) Patent No.: US 9,259,533 B2
(45) Date of Patent: Feb. 16, 2016

(54) SAFETY NEEDLE WITH SPRING BIASED RETRACTION MECHANISM

(75) Inventors: Eugene E. Weilbacher, Chesterfield, MO (US); James L. Carlyon, Farmington, MO (US)

(73) Assignee: Covidien LP, Mansfield, MA (US)

( * ) Notice: Subject to any disclaimer, the term of this patent is extended or adjusted under 35 U.S.C. 154(b) by 323 days.

(21) Appl. No.: 12/409,055

(22) Filed: Mar. 23, 2009

(65) Prior Publication Data

US 2009/0247952 A1 Oct. 1, 2009

Related U.S. Application Data

(60) Provisional application No. 61/041,021, filed on Mar. 31, 2008.

(51) Int. Cl.
*A61M 5/158* (2006.01)
*A61M 25/06* (2006.01)
*A61M 5/32* (2006.01)

(52) U.S. Cl.
CPC ............ *A61M 5/158* (2013.01); *A61M 25/0612* (2013.01); *A61M 25/0631* (2013.01); *A61M 25/0637* (2013.01); *A61M 5/3257* (2013.01)

(58) Field of Classification Search
CPC ...................... A61M 25/0612; A61M 25/0631; A61M 25/0637; A61M 5/158; A61M 5/3257; A61M 2005/1585; A61M 5/2033; A61M 5/3219; A61M 5/3232; A61M 2205/8581
USPC ......................................... 604/164.04, 164.08
See application file for complete search history.

(56) References Cited

U.S. PATENT DOCUMENTS

| | | |
|---|---|---|
| 4,183,246 A | 1/1980 | Reynolds |
| 4,676,783 A | 6/1987 | Jagger et al. |
| 4,690,675 A | 9/1987 | Katz |
| 4,747,831 A | 5/1988 | Kulli |
| 4,781,692 A | 11/1988 | Jagger et al. |
| 4,813,426 A | 3/1989 | Haber et al. |
| 4,820,282 A | 4/1989 | Hogan |
| 4,900,307 A | 2/1990 | Kulli |
| 4,900,311 A | 2/1990 | Stern et al. |
| 4,973,316 A | 11/1990 | Dysarz |
| 4,994,034 A | 2/1991 | Botich et al. |
| 5,084,030 A | 1/1992 | Byrne et al. |
| 5,085,639 A | 2/1992 | Ryan |
| 5,088,982 A | 2/1992 | Ryan |
| 5,108,376 A | 4/1992 | Bonaldo |
| 5,114,410 A | 5/1992 | Caralt Battle |

(Continued)

*Primary Examiner* — Nicholas Lucchesi
*Assistant Examiner* — Weng Lee
(74) *Attorney, Agent, or Firm* — Lisa E. Winsor, Esq.

(57) ABSTRACT

A safety needle is provided. The safety needle includes a substantially hollow body and a needle assembly that includes a needle supported on a needle hub. The needle hub is movable in relation to the hollow body from an advanced position wherein a sharp tip of the needle extends from the hollow body to a retracted position wherein the sharp tip of the needle is positioned within the hollow body. The safety needle also includes a spring biased retraction mechanism that includes a constant force spring operatively connected to the needle hub. The constant force spring is a generally flat strip of prestressed material that is formed into constant coils around itself. The constant force spring is configured to bias the needle hub towards the retracted position wherein the spring provides a substantially constant force to the needle assembly while the needle assembly moves from the advanced position to the retracted position.

13 Claims, 12 Drawing Sheets

(56) References Cited

U.S. PATENT DOCUMENTS

| | | | |
|---|---|---|---|
| 5,120,320 | A | 6/1992 | Fayngold |
| 5,125,414 | A | 6/1992 | Dysarz |
| 5,129,884 | A | 7/1992 | Dysarz |
| 5,147,327 | A | 9/1992 | Johnson |
| 5,176,655 | A | 1/1993 | McCormick et al. |
| 5,188,119 | A | 2/1993 | Sunderland |
| 5,188,599 | A | 2/1993 | Botich et al. |
| 5,192,275 | A | 3/1993 | Burns |
| 5,226,894 | A | 7/1993 | Haber et al. |
| 5,232,456 | A | 8/1993 | Gonzalez |
| 5,267,961 | A | 12/1993 | Shaw |
| 5,273,540 | A | 12/1993 | Luther et al. |
| 5,318,538 | A | 6/1994 | Martin |
| 5,330,438 | A | 7/1994 | Gollobin et al. |
| 5,338,303 | A | 8/1994 | King et al. |
| 5,376,075 | A | 12/1994 | Haughton et al. |
| 5,385,551 | A | 1/1995 | Shaw |
| 5,389,076 | A | 2/1995 | Shaw |
| 5,395,347 | A | 3/1995 | Blechet al. |
| 5,407,431 | A | 4/1995 | Botich et al. |
| 5,409,461 | A | 4/1995 | Steinman |
| 5,423,758 | A | 6/1995 | Shaw |
| 5,478,316 | A * | 12/1995 | Bitdinger et al. ............. 604/135 |
| 5,501,675 | A | 3/1996 | Erskine |
| 5,538,508 | A | 7/1996 | Steyn |
| 5,549,571 | A | 8/1996 | Sak |
| 5,554,130 | A | 9/1996 | McDonald et al. |
| 5,562,629 | A | 10/1996 | Haughton et al. |
| 5,562,634 | A | 10/1996 | Flumene et al. |
| 5,573,510 | A | 11/1996 | Isaacson |
| 5,575,777 | A | 11/1996 | Cover et al. |
| 5,578,011 | A | 11/1996 | Shaw |
| 5,591,138 | A | 1/1997 | Vaillancourt |
| 5,632,733 | A | 5/1997 | Shaw |
| 5,676,658 | A | 10/1997 | Erskine |
| 5,695,475 | A | 12/1997 | Best, Jr. et al. |
| 5,746,215 | A | 5/1998 | Manjarrez |
| 5,779,679 | A | 7/1998 | Shaw |
| 5,810,775 | A | 9/1998 | Shaw |
| 5,928,199 | A | 7/1999 | Nakagami |
| 5,931,815 | A | 8/1999 | Liu |
| 5,951,525 | A | 9/1999 | Thorne et al. |
| 5,997,512 | A | 12/1999 | Shaw |
| 6,015,438 | A | 1/2000 | Shaw |
| 6,056,726 | A | 5/2000 | Isaacson |
| 6,077,244 | A | 6/2000 | Botich et al. |
| 6,080,137 | A | 6/2000 | Pike |
| 6,090,078 | A | 7/2000 | Erskine |
| 6,096,005 | A | 8/2000 | Botich et al. |
| 6,179,812 | B1 | 1/2001 | Botich et al. |
| 6,210,371 | B1 | 4/2001 | Shaw |
| 6,221,055 | B1 | 4/2001 | Shaw et al. |
| RE37,439 | E | 11/2001 | Firth et al. |
| 6,494,863 | B1 | 12/2002 | Shaw et al. |
| 6,524,276 | B1 | 2/2003 | Halseth et al. |
| 6,547,762 | B1 | 4/2003 | Halseth et al. |
| 6,572,584 | B1 | 6/2003 | Shaw et al. |
| 6,582,402 | B1 | 6/2003 | Erskine |
| 6,620,136 | B1 | 9/2003 | Pressly, Sr. et al. |
| 6,641,555 | B1 | 11/2003 | Botich et al. |
| 6,673,047 | B2 | 1/2004 | Crawford et al. |
| 6,743,186 | B2 | 6/2004 | Crawford et al. |
| 6,773,419 | B2 | 8/2004 | Crawford et al. |
| 6,786,875 | B2 | 9/2004 | Barker et al. |
| 6,835,190 | B2 | 12/2004 | Nguyen |
| 6,860,872 | B2 | 3/2005 | Teichert |
| 6,905,478 | B2 | 6/2005 | Ingram et al. |
| 6,929,624 | B1 * | 8/2005 | Del Castillo ............. 604/164.12 |
| 6,942,652 | B1 | 9/2005 | Pressly et al. |
| 6,945,960 | B2 | 9/2005 | Barker et al. |
| 6,972,002 | B2 | 12/2005 | Thorne |
| 6,976,976 | B2 * | 12/2005 | Doyle ............................ 604/198 |
| 7,037,292 | B2 | 5/2006 | Carlyon et al. |
| 7,422,572 | B2 | 9/2008 | Popov et al. |
| 7,611,486 | B2 * | 11/2009 | Jones et al. .................... 604/110 |
| 2003/0040717 | A1 | 2/2003 | Saulenas et al. |
| 2003/0078540 | A1 * | 4/2003 | Saulenas et al. .............. 604/110 |
| 2003/0093035 | A1 | 5/2003 | Mohammed |
| 2003/0199830 | A1 | 10/2003 | Nguyen |
| 2003/0220619 | A1 | 11/2003 | Polidoro et al. |
| 2004/0193110 | A1 | 9/2004 | Giambattista et al. |
| 2004/0267200 | A1 | 12/2004 | Carlyon et al. |

\* cited by examiner

SAFETY NEEDLE WITH SPRING BIASED RETRACTION MECHANISM

CROSS REFERENCE TO RELATED APPLICATION

This patent application claims priority to U.S. Provisional Application Ser. No. 61/041,021, filed Mar. 31, 2008, which is incorporated herein in its entirety by reference.

BACKGROUND

1. Technical Field

The present disclosure relates to retractable safety needles. More particularly, the present disclosure relates to retractable safety needles incorporating a spring biased retraction mechanism that provides a constant force to an associated needle assembly during retraction of the needle assembly.

2. Background of Related Art

Hypodermic needles are used for venous access in a variety of medical procedures including fluid sampling, percutaneous medication injection, and other fluid delivery or withdrawal procedures. Some of the health risks associated with hazardous needle exposure includes HIV, hepatitis, and other blood-borne pathogens. Medical professionals are in danger of contracting such blood-borne pathogens from infected patients by inadvertent needle sticks from needles contaminated during medical procedures.

Various protective devices including sheaths, have been used to shield sharp tips of needles in order to alleviate danger of needlestick injury to a user. Additionally, many needle devices include the provision of an automatic retraction system to shield the needle within a housing associated with the needle assembly after use.

Commercially available needle devices that include the provision of an automatic retraction system typically rely on the use of compression springs to provide the needed retraction forces. The compression springs utilized by these systems provide high forces at full compression of the spring and little or no force at full extension of the spring. As a result, extreme force changes are present when the needle is moved from an extended position to a retracted position, which, in turn may result in accidental needlestick injuries, blood splattering, or other undesirable outcomes. In addition, compression springs are bulky and, thus, may require an increase in the cross-section of the needle device to accommodate the spring.

Therefore, it would be desirable to provide a safety needle device which includes a spring mechanism that provides a constant force throughout retraction and/or extension of the needle. It would be further desirable to provide a spring mechanism which is simple, low-cost, and can be easily incorporated into existing safety needle devices.

SUMMARY

The presently disclosed safety needle is configured for use in intravenous procedures. The present disclosure provides a safety needle that includes a substantially hollow body and a needle assembly that includes a needle supported on a needle hub. The needle hub is movable in relation to the hollow body from an advanced position wherein a sharp tip of the needle extends from the hollow body to a retracted position wherein the sharp tip of the needle is positioned within the hollow body. The safety needle also includes a spring biased retraction mechanism that includes a constant force spring operatively connected to the needle hub. The constant force spring is configured to bias the needle hub towards the retracted position wherein the spring provides a substantially constant force to the needle assembly while the needle assembly moves from the advanced position to the retracted position. In embodiments, the spring includes one or more apertures configured to connect to one or more protrusions that are located on a surface of the hub. In embodiments, the spring is positioned within a cavity defined by the hollow body and located at a proximal end thereof. The cavity includes a cradle for supporting the spring. In embodiments, the spring is coiled around a drum. Alternatively, the spring may be around itself. In embodiments, the spring is made from metal. In embodiments, the spring is made from type 301 stainless steel.

In embodiments, the spring is located on a bottom side of the body and is configured such that fluid flow through a proximal end of a transparent fluid tube may be observed through a transparent top side of the body. Here, the spring includes a light colored surface finish that provides a contrasting background for observing fluid flow through the tube.

In embodiments, the spring includes one or more slots and is located on a top side of the body such that fluid flow through a proximal end of a transparent fluid tube may be observed through a transparent top side of the body.

DESCRIPTION OF THE DRAWINGS

Various embodiments of the presently disclosed safety needle are disclosed herein with reference to the drawings, wherein.

DETAILED DESCRIPTION OF EMBODIMENTS

Embodiments of the presently disclosed safety needle with spring biased retraction mechanism will now be described in detail with reference to the drawings wherein like numerals designate identical or corresponding elements in each of the several views. As is common in the art, the term "proximal" refers to a location on the device closer to the user or operator, i.e. surgeon or physician, while the term "distal" refers to a location on the device further away from the user.

The present disclosure provides a spring biased retraction mechanism that includes a spring operatively connected to a hub of a safety needle. The spring is configured to provide a constant force throughout retraction of the needle device. With this purpose in mind, the spring employed is a constant force spring.

Figure 1:
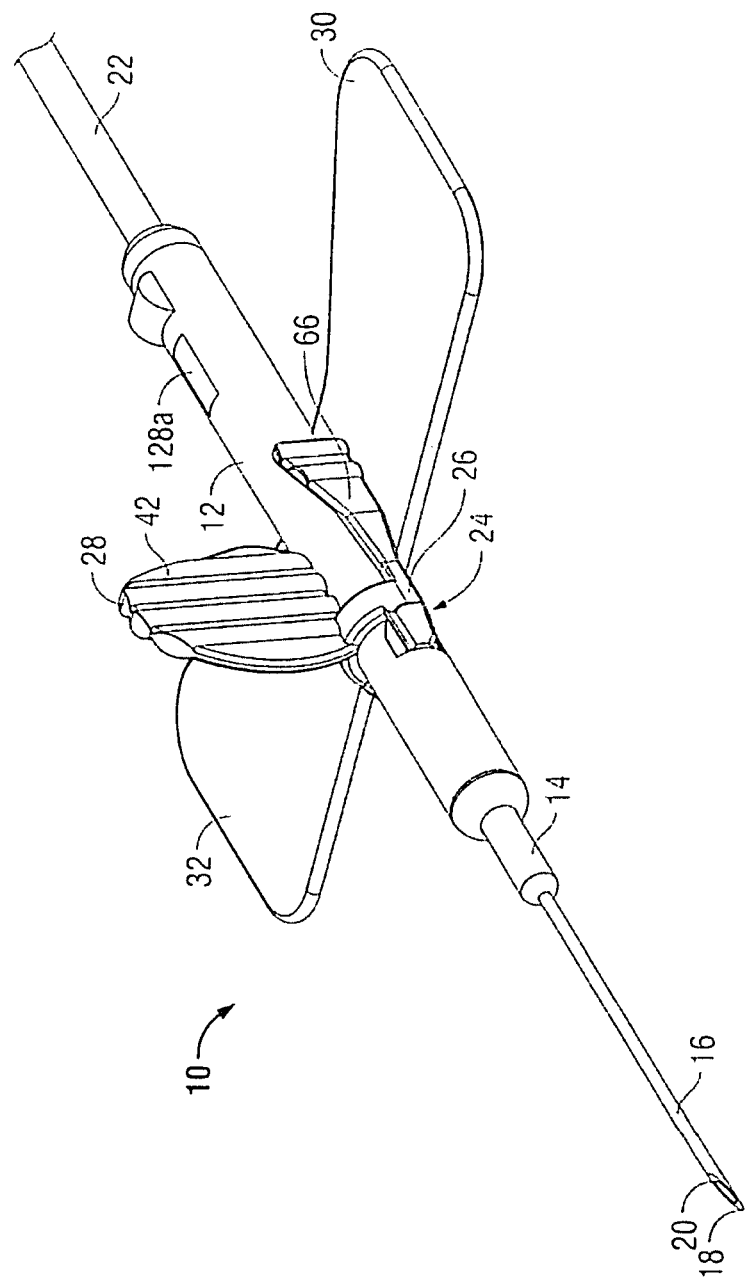
FIG. 1 is a perspective view of one embodiment of the presently disclosed safety needle with a retraction mechanism that employs a constant force spring with a needle in an extended position.
Figure 2:
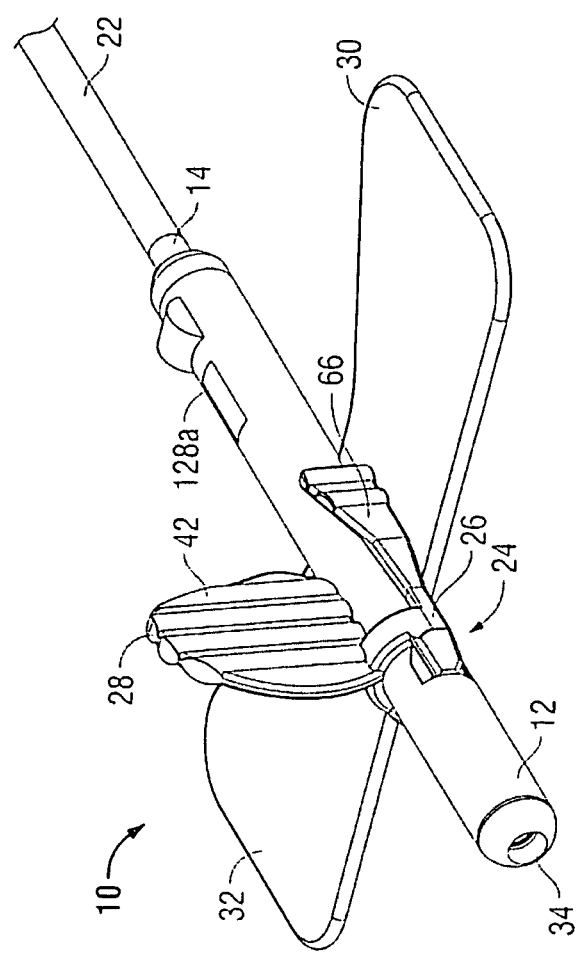
FIG. 2 is a perspective view of the safety needle shown in FIG. 1 with the needle in a retracted position.
Figure 3:
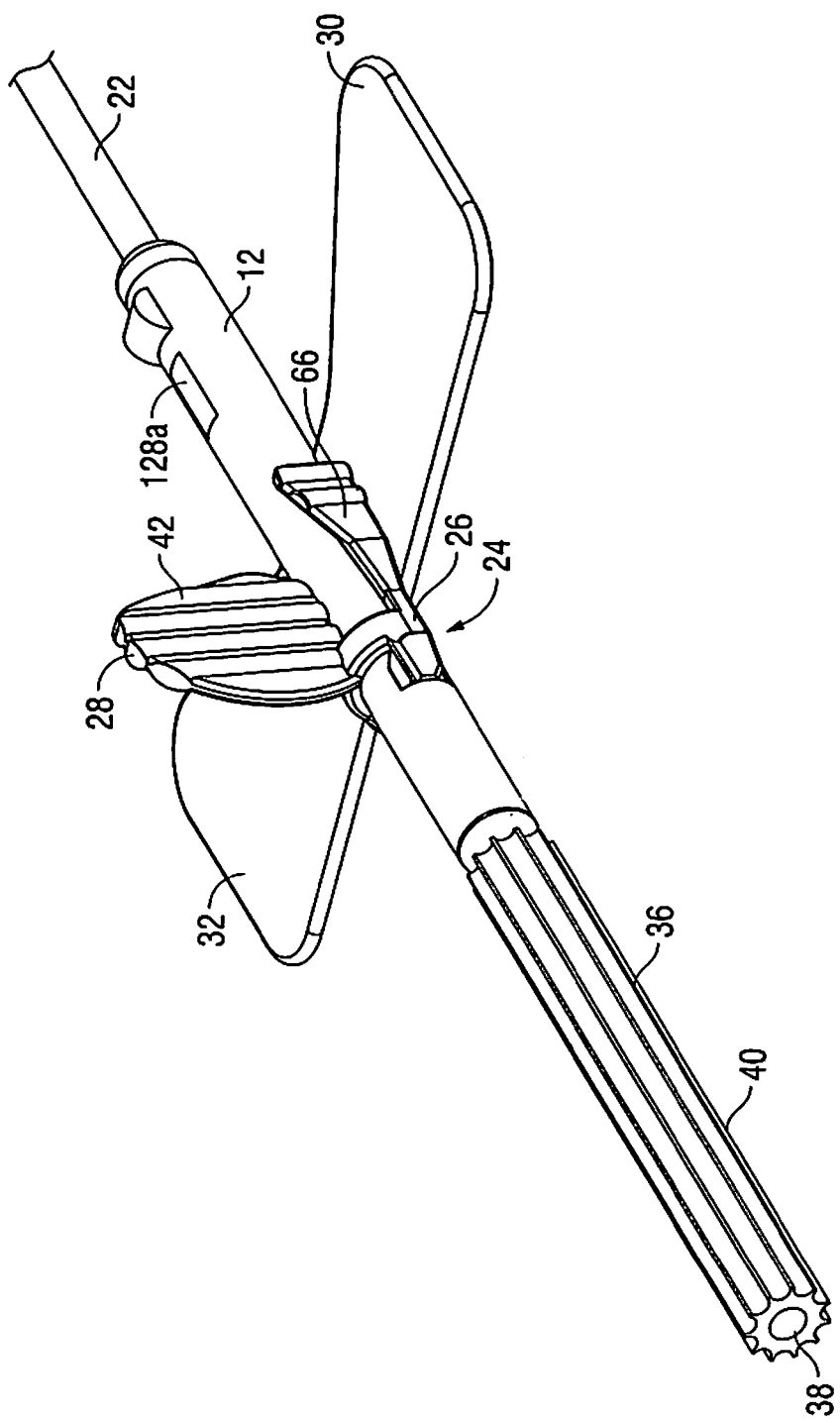
FIG. 3 is a perspective view of the safety needle shown in FIG. 1 with a safety sheath positioned about the needle.
Figure 6:
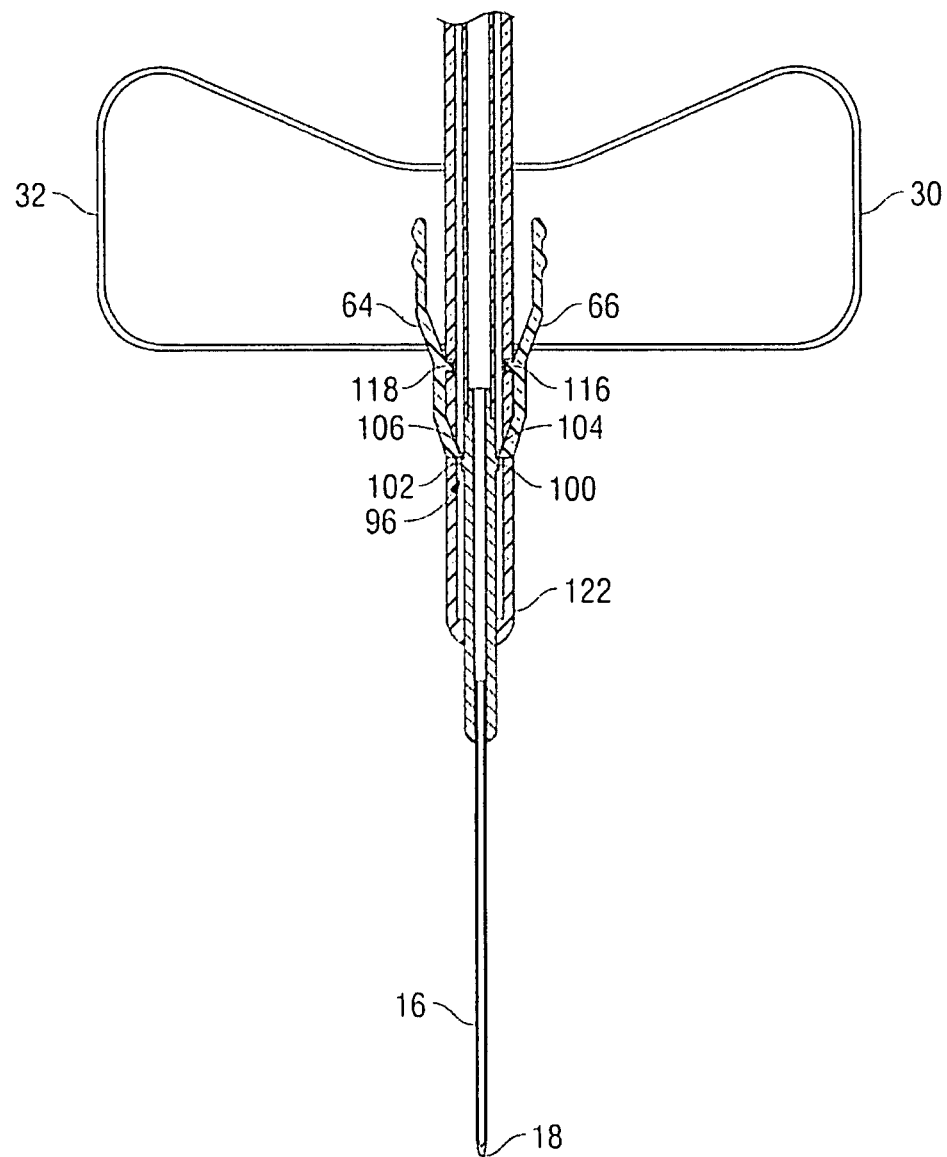
FIG. 6 is a top cross-sectional view of the safety needle shown in FIG. 1 with the needle in the extended position.
Figure 9:
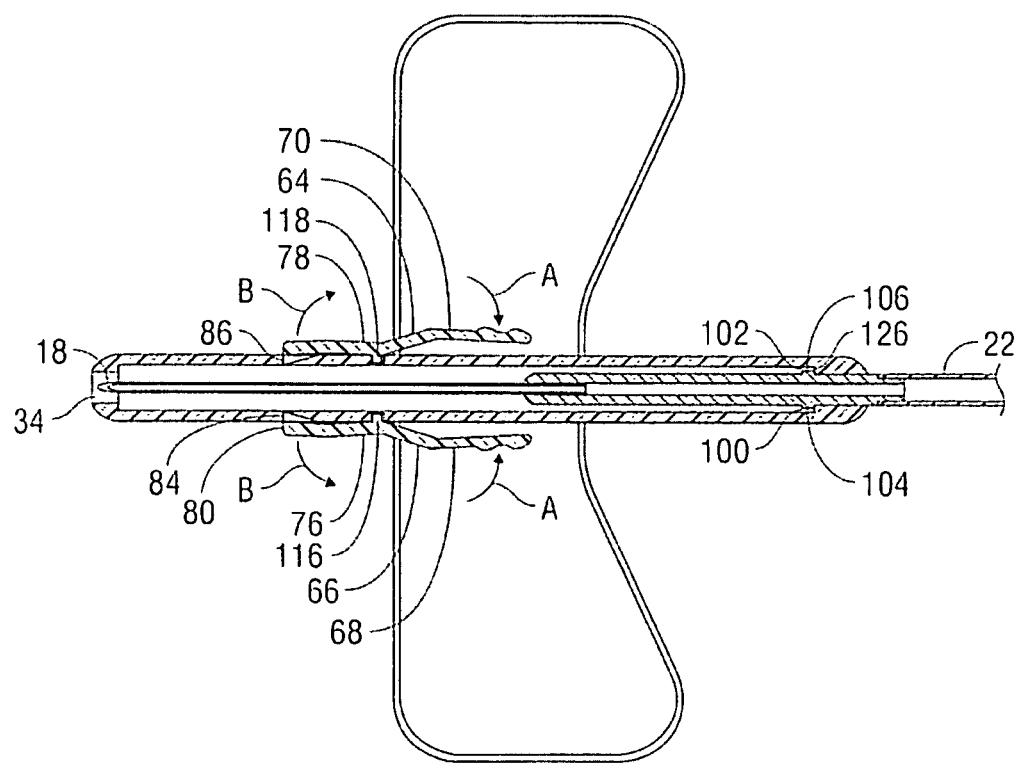
FIG. 9 is a top cross-sectional view of the safety needle shown in FIG. 1 with the needle nearing the fully retracted position.

Referring now to FIGS. 1-3, and initially with regard to FIG. 1, there is disclosed one embodiment of a safety needle 10 that may employ the spring biased retraction mechanism 24 of the present disclosure. Safety needle 10 is of the type generally used during intravenous procedures to insert or withdraw fluid from the body of a patient. Generally, safety needle 10 includes an elongated tubular housing or body 12, a needle hub 14 and a hollow needle or cannula 16. Needle 16 extends distally from hub 14 and has a sharp tissue penetrating tip 18 at a distal end 20 of needle 16. Needle 16 is supported on and movable with hub 14 in relation to the body 12 from an extended position (FIG. 1) to a retracted position (FIG. 9). In the retracted position, needle 16 is positioned within body 12 to shield a user from sharp tip 18 of needle 16. A fluid tube 22 extends from a proximal end of hub 14 through a proximal end of body 12 and is in fluid communication with needle 16 through hub 14 (FIG. 6). Fluid tube 22 may be transparent.

Safety needle 10 includes retraction mechanism 24 to move needle 16 from the extended position to the retracted position. A release member 26 of retraction mechanism 24 enables a user to actuate retraction mechanism 24 as will be described in further detail below.

Safety needle 10 optionally includes a dorsal fin 28 to facilitate manipulation of safety needle 10 by a user during insertion or withdrawal of needle 16 from a patient. Dorsal fin 28 may be integrally formed with release member 26 or, alternatively, can be affixed to, or integral with, body 12 (renumbered fin 30 to 28 in FIG. 2).

Safety needle 10 also includes a pair of wings 30, 32 which stabilize safety needle 10 against the body of the patient. Wings 30, 32 may be either flexible or rigid and may be formed separately from, or integral with, elongate tubular member 12. One or both of wings 30, 32 may be used to facilitate grasping of safety needle 10 during insertion and withdrawal of needle 16 from the body of a patient.

In FIG. 2, safety needle 10 is illustrated with needle 16 in the retracted position. In the retracted position, needle 16 is safely contained within a bore 34 of body 12. In the retracted position, body 12 minimizes the risk of needle stick injury to the user as will be described in more detail hereinbelow.

Referring also to FIG. 3, safety needle 10 is illustrated with a safety sheath 36 positioned over needle 16. Safety sheath 36 includes a bore 38 which is dimensioned to receive needle 16. Safety sheath 36 is designed to protect a user from needle stick injury prior to use of safety needle 10. Safety sheath 36 may include a ribbed outer surface 40 to facilitate grasping and removal of safety sheath 36 from body 12 by the user. It is contemplated that safety needle 10 will be shipped with safety sheath 36 positioned over needle 16 to prevent needle-stick injury to the user prior to its use in a medical procedure.

In order to facilitate manipulation of safety needle 10, dorsal fin 28 may also be provided with a ribbed outer surface 42 to provide a secure grasping surface to be gripped by the user. It is contemplated herein that safety needle 10 may be provided with other textured or ribbed services to facilitate manipulation by the user, e.g., knurled, grooved, etc.

Figure 4:
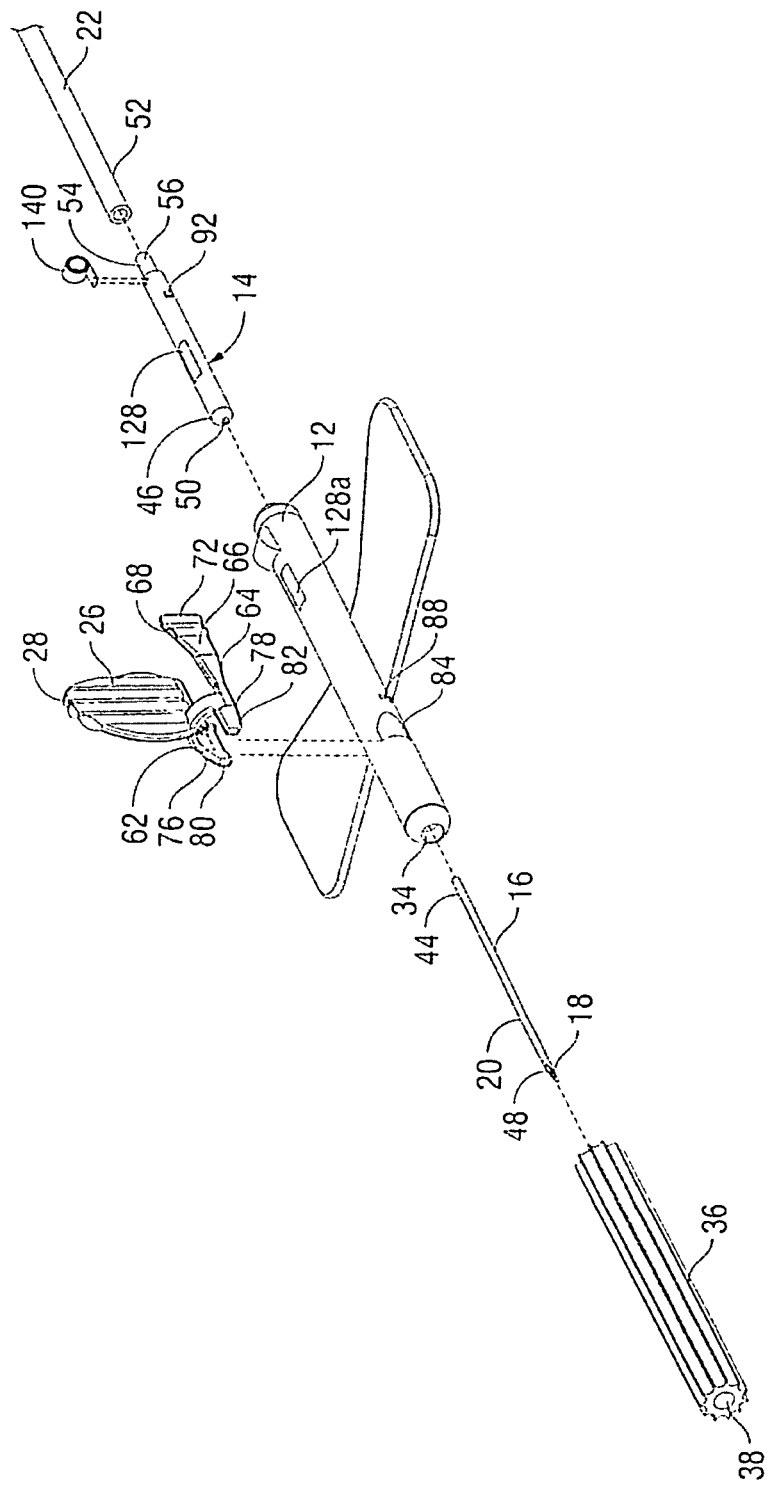
FIG. 4 is a perspective view of the safety needle shown in FIG. 3 with parts separated.
Figure 5:
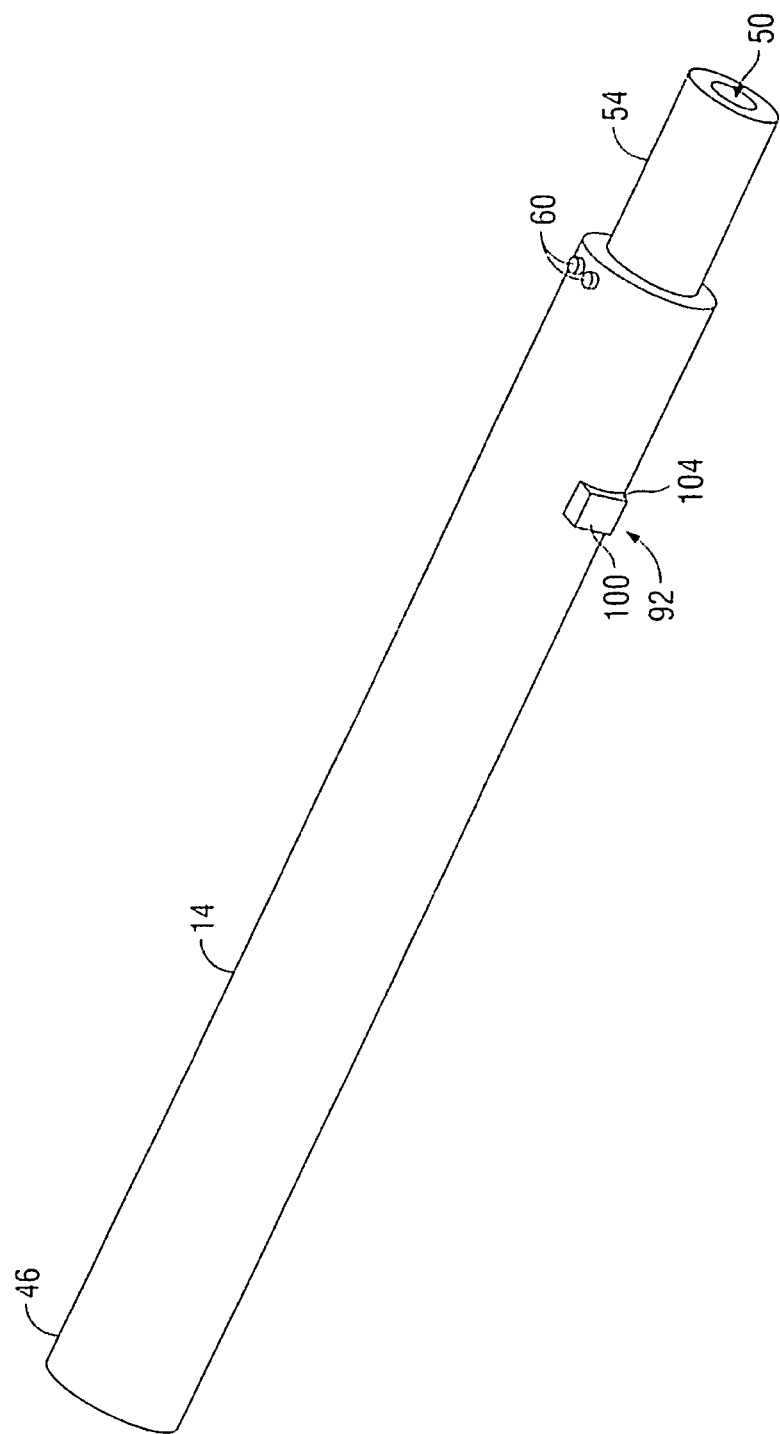
FIG. 5 is a perspective view of a hub of the safety needle shown in FIG. 1.

Referring now to FIGS. 4 and 5, safety needle 10 will now be described in more detail. The proximal end 44 of needle 16 extends through bore 34 of elongate body 12 and is affixed to a distal end 46 of hub 14. As noted above, needle 16 is of the type used during intravenous procedures and includes a throughbore 48 for the transmission of fluids. Hub 14 similarly includes a throughbore 50 for transmission of fluids between needle 16 and fluid tube 22. A first end 52 of fluid tube 22 is affixed over a stepped down portion 54 formed at a proximal end 56 of hub 14.

Figure 7:
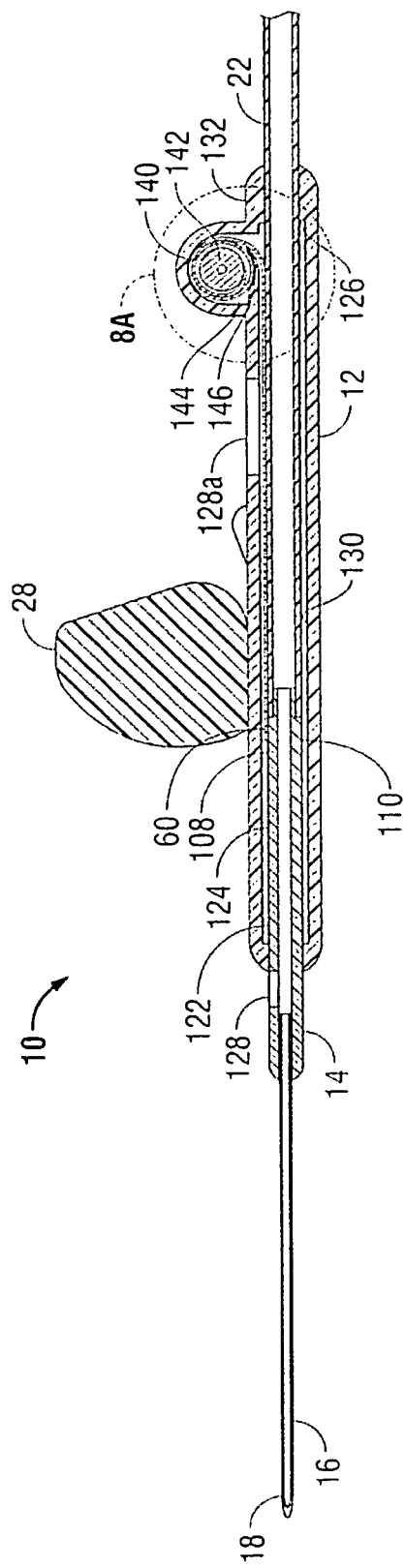
FIG. 7 is a side cross-sectional view of the safety needle shown in FIG. 6 with the needle in the extended position.

Referring also to FIG. 7, safety needle 10 includes a retraction mechanism 24 to retract needle 16 into through bore 34 of body 12 to prevent needlestick injury to the user. Retraction mechanism 24 includes a spring 140 which is positioned proximally within a cavity 144 defined in body 12. Spring 140 is configured to engage one or more protrusions 60 formed on hub 14 to bias hub 14, and thus needle 16, proximally within body 12 in a manner described in more detail hereinbelow. Alternatively, it is envisioned that a variety of different fastening techniques can be used to fasten spring 140 to hub 14, e.g., pins, screws, moldings, rivets etc.

Referring to FIGS. 1-4 and 6, 7 and 9, release member 26 includes a bridge 62 having a first arm 64 and a second arm 66 positioned on opposite sides of bridge 62. Arms 64 and 66 are flexible about bridge 62. Arm 64 includes a proximal arm section 68 and arm 66 includes a proximal arm section 70 (FIG. 9). Proximal arm sections 68 and 70 are configured to be grasped by the user in order to actuate release member 26. Proximal arm sections 68, 70 include ribbed surfaces 72, 74 respectively, to facilitate grasping by the user. Arms 64, 66 include distal arm portions 76, 78, respectively which are configured to engage hub 14 and retain hub 14 in an advanced or a distal most position within body 12 against the bias of spring 140. Specifically, distal arm portion 76 includes a lip 80 and distal arm portion 78 includes a lip 82. Distal arms 76 and 78 extend through a pair of cut outs 84, 86 (86 is now shown) (FIGS. 4 and 9) formed in opposite sides of body 12 such that lips 80, 82 project into bore 34 of body 12. Release member 26 is supported on body 12 in snap fit fashion. A pair of notches 88, 90 is formed on opposite sides of body 12 to retain release member 26 thereon and to provide pivot points for arms 64, 66.

Referring to FIG. 5, hub 14 is provided with stop structure 92 which is positioned to engage lips 80, 82 of arm portions 76 and 78 such that lips 80, 82 retain hub 14 in an extended position within body 12 against the bias of spring 140. Hub 14 is provided with one or more protrusions 60 (two protrusions are shown). As noted above, protrusions 60 are provided to engage a distal end of spring 140 in order to bias hub 14 towards the retracted position. Protrusions 60 are configured and dimensioned to be received in one or more corresponding apertures 148 located on a distal end of spring 140 such that hub 14 and spring 140 are maintained in a connected condition, e.g., press fit. Alternatively, or in addition to protrusions 60, hub 14 may have a slit or other suitable structure (not explicitly shown) configured to engage with spring 140. Further, hub 14 and spring 140 may be connected by way of stamping, overmolding, injection molding and so on. The manner in which spring 140 and hub 14 are connected is not critical to the operation of safety needle 10, as described herein.

In order to retain hub 14 in an extended position against the bias of spring 140, stop structure 92 on hub 14 includes a first engagement block 100 and a second engagement block 102 provided on an opposite side of hub 14. Engagement blocks 100, 102 are provided with proximally facing engaging surfaces 104 and 106. When hub needle 16 is in an extended or advanced position, engaging surfaces 104 and 106 of blocks 100 and 102 of hub 14 are engaged by a lips 80, 82 of arms 64 and 66, respectively, of release member 26 to retain hub 14 in the advanced position. Proximally facing engaging surfaces 104 and 106 provide the further function of limiting the extent of retraction of hub 14 within body 12 in a manner described in more detail hereinbelow. Alternatively, blocks 100 and 102 could be removed and a collar or other projection configuration (not explicitly shown) may function to engage lips 80, 82 of release member 26 and limit retraction of hub 14 within body 12.

Referring now to FIG. 6, as noted above, arms 64 and 66 are pivotally mounted to body 12. Specifically, arms 64 and 66 are provided with pivot projections 116 and 118. Pivot projections 116, 118 are configured to reside within notches 88 and 90 (FIG. 4) formed in body 12. Pivot projections 116, 118 secure release member 26 both circumferentially and longitudinally to body 12.

Figure 8A:
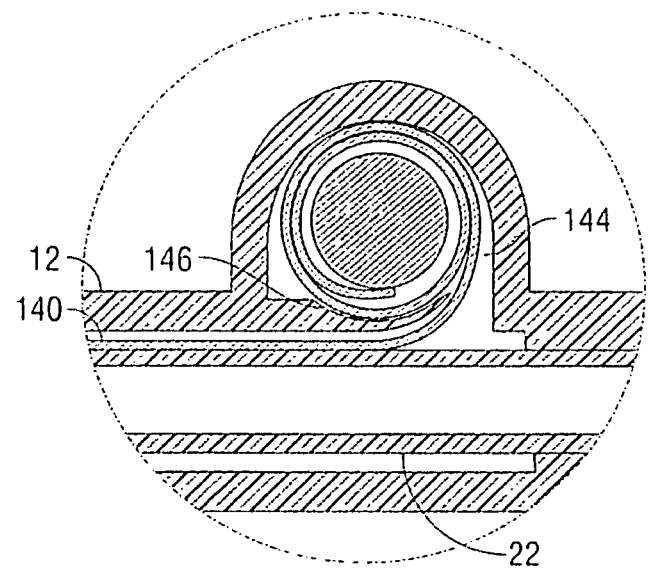
FIG. 8A is an enlarged view of the indicated area of detail shown in FIG. 7.
Figure 8B:
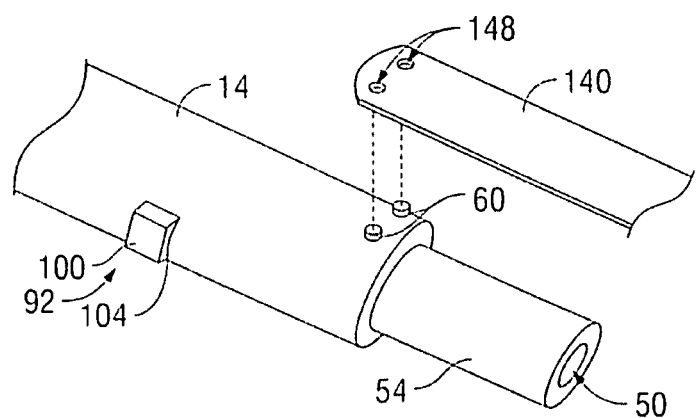
FIG. 8B is a side perspective cutaway view of a distal portion of the constant force spring positioned above the proximal portion of the hub of the safety needle shown in FIG. 1.

With reference now to FIGS. 7-8B, spring 140 is configured to provide a substantially constant force to hub 14 while hub 14 moves from the extended or advanced position to the retracted position. To this end, spring 140 is a constant force extension spring. Constant force extension springs typically are prestressed into flat strips of spring material that are formed into constant radius coils. These types of springs produce constant force which makes them suitable for use with the retraction mechanism 24 of the present disclosure. Suitable commercially available constant force extension springs are manufactured and sold by AMETEK, Inc. under the trademark NEG'ATOR®.

Figure 10A:
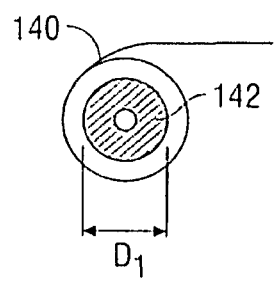
FIG. 10A is a side view illustrating the constant force spring shown in FIG. 8A coiled around a suitable drum.
Figure 10B:
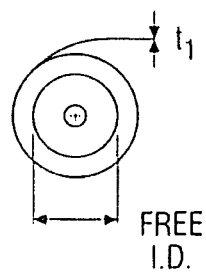
FIG. 10B is a side view illustrating the constant force spring shown in FIG. 8A coiled around itself.

As shown, spring 140 is coiled around a drum 142 (FIG. 10A). Alternatively, spring 140 may be coiled around itself (FIG. 10B). Spring 140 may be made from any suitable material including metal, metal alloys, plastic, and so on. In embodiments, spring 140 is made from type 301 stainless steel. Prior to formation, spring 140 may be annealed to improve the cold working properties of the steel. Spring 140 may also be treated chemically or otherwise.

Spring 140 resides within a cavity 144 located at a proximal end of body 12, as best shown in FIG. 8A. Cavity 144 may be formed separately from, or integral with, body 12. Cavity 144 is configured and dimensioned such that spring 140 is free to recoil (retraction) as needed. To this end, an arcuate surface forms a cradle 146 that extends into cavity 144 of body 12. Cavity 144 is provided with an opening configured such that spring 140 may extend within body 12. Cradle 146 provides support for spring 140 to facilitate recoiling of spring 140. Cavity 144 may include one or more brackets and/or axels that extend laterally within cavity 144 (not explicitly shown). The brackets and/or axels provide additional support for spring 140. Additionally, the brackets and/or axels may be used to support spring 140 in an elevated or suspended configuration, which may facilitate recoiling of the spring 140. In this manner, cradle 146 may be eliminated.

Figure 10C:
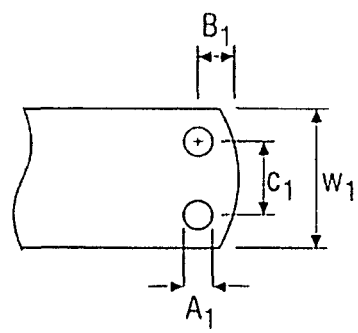
FIG. 10C is a top view illustrating the constant force spring shown in FIG. 8B with two apertures.

Referring to FIGS. 8B and 10C, spring 140 is operatively connected to hub 14 by engagement of protrusions 60 of hub 14 within apertures 148 of spring 140 as discussed above. Apertures 148 are disposed on spring 140 such that apertures 148 align along the same central axis as protrusions 60. Apertures 148 have diameters $A_1$ (FIG. 10C), that are large enough to fit around protrusions 60 such that spring 140 remains connected to hub 14 during advancement and retraction of hub 14. Further, protrusions 60 may extend through and beyond apertures 148 to enable heat staking.

The dimensions of spring 140 may vary depending on, inter alia, space, life cycle, load, and/or operation requirements of the surgical needle 10 that spring 140 is configured for use with.

With reference again to FIG. 9, body 12 has a proximal facing surface 126 within bore 34 which cooperates with proximal facing surfaces 104 and 106 of engagement blocks 100, 102 to limit the proximal travel of hub 14 within body 12.

Figure 11A:
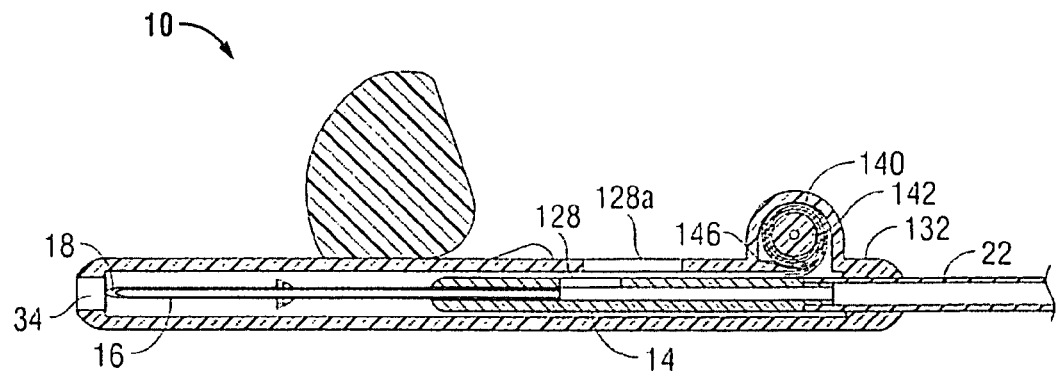
FIG. 11A is a side cross sectional view of the safety needle shown in FIG. 9 with the needle in the fully retracted position.
Figure 11B:
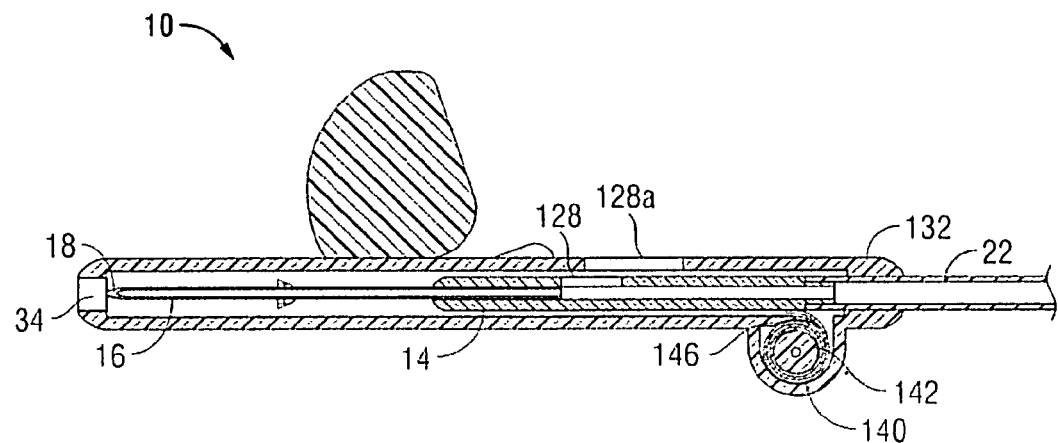
FIG. 11B is a side cross sectional view of a safety needle with the needle in the fully retracted position and the spring located on a bottom side of the body in accordance with another embodiment of the present disclosure.
Figure 11C:
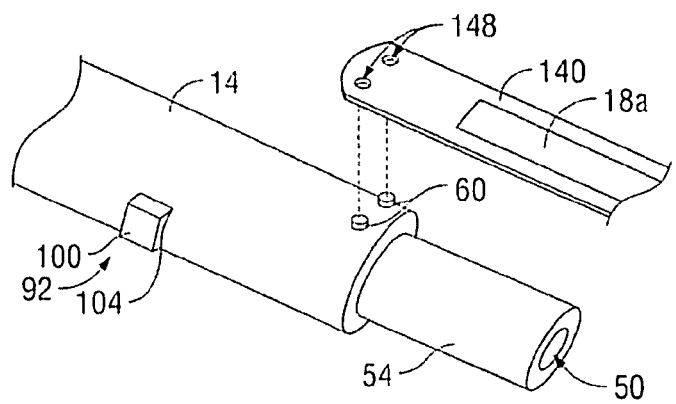
FIG. 11C is a side perspective cutaway view of a distal portion of the constant force spring in accordance with another embodiment of the present disclosure.

In order to observe the flow of fluids through hub 14, hub 14 is provided with a transparent zone 128 (FIGS. 4 and 7) at a distal end adjacent the proximal end of needle 16 (zone 128 was moved to right in drawings as suggested). By observing the flow of fluid through transparent zone 128, the user can confirm that needle 16 has been properly positioned within the body. Alternatively, hub 14 and/or body 12 may be made from a transparent material. Further, at least a top side of body 12 (portion facing user) may be provided with a transparent zone, or aperture, 128a and configured for observation of fluid flow through tube 22 and/or hub 14. It is also envisioned that spring biased retraction mechanism 24 may be located on the bottom side (FIG. 11B) or lateral portions (not explicitly shown) of body 12 such that the flow of fluids through the proximal end of transparent fluid tube 22 may be more easily observed through the transparent top side of body 12. Spring 140 may possess a light colored surface finish (e.g. white) to provide a contrasting background for observing fluid flow through tube 22 and/or hub 14. Additionally, especially with spring based mechanism 24 located on the top side of body 12, spring 140 may include at least one additional aperture, slot, or void 148a located along a length thereof (FIG. 11C) to facilitate observation of fluid flow through tube 22 and/or hub 14.

With reference to FIGS. 3 and 6, 7, 8, and 11, the use and operation of safety needle 10 will now be described. As best shown in FIG. 3, safety needle 10 is provided with safety sheath 36 positioned over needle 16 to prevent any needle-stick injury to the user during shipping, unpackaging and immediately prior to use of safety needle 10. Once the user is ready to employ safety needle 10, ribbed outer surface 40 of safety sheath 36 is grasped and safety sheath 36 is removed from needle 16 (Referential numerals 36, 40 now conform with drawings).

Referring now to FIGS. 6 and 7, in the initial position, needle 16 is in the advanced position and extends distally from body 12. Spring 140 is in an extended uncoiled condition along inner surface 122 of body 12. Hub 14 is retained in the advanced position by engagement of lips 80, 82 with proximal facing surfaces 104 and 106 of engagement blocks 100,102 (FIG. 6).

Figure 12:
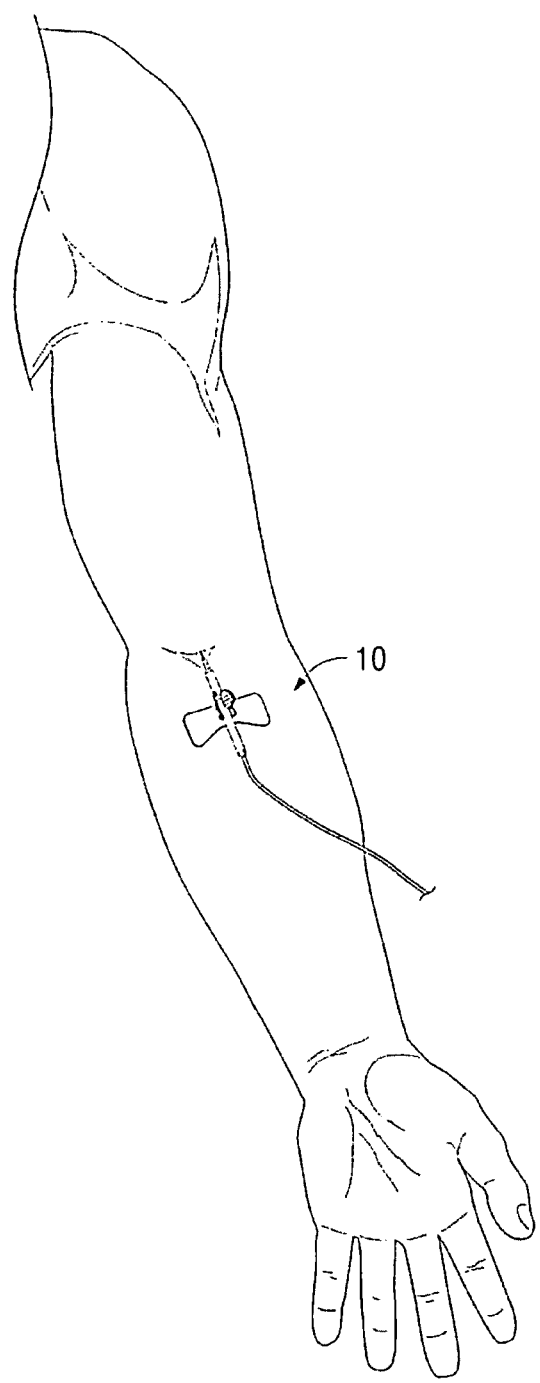
FIG. 12 is a perspective view of the safety needle shown in FIG. 1 with the needle in the extended position inserted into the arm of a patient.

Once safety needle 10 has been unpackaged and safety sheath 36 removed, safety needle 10 is inserted in normal intravenous fashion into a patient such that sharp tip 18 penetrates a vein for infusion, injection and/or removal of fluids from a patient (See FIG. 12). In order to assist in the insertion of needle 16 of safety needle 10 into the vein of a patient, the user may grasp dorsal fin 28 which is provided to facilitate manipulation of safety needle 10. Alternatively, one or both wings 30 and 32 may be grasped to facilitate insertion of safety needle 10 into a vein. Once safety needle 10 has been inserted into the vein of a patient, the proper positioning of needle 16 within the vein may be verified by observing the flow of fluids through transparent portion 128 of hub 14 or the otherwise as noted above.

Referring now to FIG. 9, once the intravenous procedure has been completed, the user can leave needle 16 within the vein of the patient or remove needle 16 from the body of the patient. Again, dorsal fin 28 or one or more wings 30, 32 can be grasped to facilitate removal of safety needle 10 from the body of the patient. When so desired, the user may actuate retraction mechanism 24 to retract sharp tip 18 of needle 16 safely within bore 34 of body 12. Retraction mechanism 24 is actuated by squeezing proximal arm 68 and proximal arm 70 inwardly towards body 12 in the direction indicated by arrows A in FIG. 9 to rotate arms 64 and 66 about pivot points 116, 118. This rotation of arms 64 and 66 moves distal arms 76 and 78 radially outwardly in the direction indicated by arrows B in FIG. 9. As distal arms 76 and 78 move outwardly, lips 80 and 82 disengage from proximal facing surfaces 104 and 106 of engagement blocks 100, 102.

Once lips 80, 82 have been disengaged from engagement blocks 100, 102, hub 14 is free to move in a proximal direction in response to the bias of spring 140. As noted above, because spring 140 is a constant force spring, hub 14 will be provided with a constant force throughout retraction. In this manner, retraction of sharp tip 18 from the vein of the patient will occur with minimal trauma and/or proximal movement of needle 16 will result in minimal splatter. Hub 14 will move proximally until proximally facing surfaces 104 and 106 engage proximal inner surface 126 of tubular body 12. This prevents any further proximal retraction of hub 14 relative to body 12.

As shown, in the proximal most position sharp tip 18 of needle 16 is safely contained within bore 34 of body 12 to prevent needlestick injury to the user.

It will be understood that various modifications may be made to the embodiments disclosed herein. For example, safety needle 10 may include a lockout structure which retains needle 16 in a retracted position within body 12 and prevents re-advancement thereof. Although the presently disclosed retraction mechanism including a constant force spring is described in association with a winged intravenous needle assembly, it is envisioned that the retraction mechanism could be incorporated into any existing retractable needle assembly including retractable needle syringes. Therefore, the above description should not be construed as limiting, but merely as exemplifications of particular embodiments. Those skilled in the art will envision other modifications within the scope and spirit of the claims appended hereto.

The invention claimed is:

1. A safety needle comprising:
   a substantially hollow body having a central longitudinal axis;
   a needle assembly including a needle supported on a needle hub, the needle hub being movable in relation to the hollow body along the longitudinal axis from an advanced position wherein a sharp tip of the needle extends from the hollow body to a retracted position wherein the sharp tip of the needle is positioned within the hollow body; and
   a spring biased retraction mechanism including a constant force spring operatively connected to the needle hub, the constant force spring being a generally flat strip of pre-stressed material that is coiled around itself, the constant force spring being configured to bias the needle hub towards the retracted position wherein the spring provides a substantially constant force to the needle assembly while the needle assembly moves from the advanced position to the retracted position, wherein the constant force spring is positioned within a cavity defined by the hollow body at a proximal end of the hollow body, the cavity being offset from the longitudinal axis of the hollow body, wherein when the needle assembly is in the advanced position a portion of the constant force spring extends along an interior surface of the hollow body outside the cavity.

2. The safety needle as recited in claim 1, wherein the spring includes at least one aperture configured to connect to at least one protrusion located on a surface of the needle hub.

3. The safety needle as recited in claim 1, wherein the cavity includes a cradle for supporting the spring.

4. The safety needle as recited in claim 1, wherein the spring is coiled around a drum.

5. The safety needle as recited in claim 1, wherein the spring is made from a metal.

6. The safety needle as recited in claim 5, wherein the spring is made from type 301 stainless steel.

7. The safety needle as recited in claim 1, further including a transparent fluid tube connected to the needle hub, the transparent fluid tube being positioned to be observed through a transparent zone of the body.

8. A safety needle comprising:
   a substantially hollow body;
   a needle assembly including a needle supported on a needle hub, the needle hub being movable in relation to the hollow body from an advanced position wherein a sharp tip of the needle extends from the hollow body to a retracted position wherein the sharp tip of the needle is positioned within the hollow body; and
   a spring biased retraction mechanism including a constant force spring operatively connected to the needle hub, the constant force spring being a generally flat strip of pre-stressed material that is coiled around itself, the constant force spring being configured to bias the needle hub towards the retracted position wherein the spring provides a substantially constant force to the needle assembly while the needle assembly moves from the advanced position to the retracted position, wherein the constant force spring is positioned within a cavity defined by the hollow body at a proximal end of the hollow body, the cavity including a cradle for supporting the spring, the cradle comprising an arcuate surface extending into the cavity;
   wherein the spring is positioned such that an axis about which the spring is coiled is perpendicular to a direction of travel of the needle hub, and a coiled end of the spring is stationary with respect to the hollow body.

9. The safety needle as recited in claim 8, wherein when the needle assembly is in the advanced position a portion of the constant force spring extends along an interior surface of the hollow body outside the cavity.

10. The safety needle as recited in claim 1, wherein the constant force spring is directly connected to the needle hub.

11. The safety needle as recited in claim 3, wherein a portion of the constant force spring extends below the cradle.

12. The safety needle as recited in claim 3, wherein the cradle comprises an arcuate surface extending into the cavity.

13. The safety needle as recited in claim 3, wherein the cradle is positioned above the longitudinal axis of the hollow body.

* * * * *